US008835637B2

(12) United States Patent
Cysewski et al.

(10) Patent No.: US 8,835,637 B2
(45) Date of Patent: Sep. 16, 2014

(54) IRIDIUM-BASED COMPLEXES FOR ECL

(71) Applicant: Roche Diagnostics Operations, Inc., Indianapolis, IN (US)

(72) Inventors: Robert Cysewski, Chojnice (PL); Luisa de Cola, Strasbourg (FR); Jesus Miguel Fernandez Hernandez, Muenster (DE); Hans-Peter Josel, Weilheim (DE); Eloisa Lopez-Calle, Ludwigshafen (DE); Toralf Zarnt, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/961,401

(22) Filed: Aug. 7, 2013

(65) Prior Publication Data

US 2013/0323719 A1 Dec. 5, 2013

Related U.S. Application Data

(63) Continuation of application No. PCT/EP2012/051996, filed on Feb. 7, 2012.

(30) Foreign Application Priority Data

Feb. 9, 2011 (EP) ..................... 11153913

(51) Int. Cl.
*C07F 15/00* (2006.01)
*G01N 33/533* (2006.01)
(52) U.S. Cl.
CPC .......... *C07F 15/0033* (2013.01); *G01N 33/533* (2013.01)
USPC ................................ 546/4; 546/10
(58) Field of Classification Search
USPC ...................................... 546/4, 10
See application file for complete search history.

(56) References Cited

U.S. PATENT DOCUMENTS 5,219,847 A 6/1993 Taguchi et al.

FOREIGN PATENT DOCUMENTS

| EP | 0404097 A2 | 12/1990 |
| EP | 1418 217 A1 | 5/2004 |
| JP | 2007-169474 A * | 7/2007 ............. C09K 11/06 |
| WO | 93/01161 A1 | 1/1993 |
| WO | 2005/118606 A1 | 12/2005 |

OTHER PUBLICATIONS

Lion, C. et al., "Synthesis in the Phenanthridine Series I. Search for Optimum Experimental Conditions in the Preparation of 6-Alkylphenanthridines and of the Salt Thereof," Bull. Soc. Chim. Belg, 1989, pp. 557-566, vol. 98, No. 8, English translation.
International Search Report issued Mar. 13, 2012 in Application No. PCT/EP20121051996, 3 pages.
Cymerman, J. and Short, W. F., "150. Amidines. Part XII. Preparation of 9-Substituted Phenanthridines from N-2-Diphenylylamidines," Journal of the Chemical Society, 1949, pp. 703-707.
Holliger, Philipp et al., "Diabodies': Small bivalent and bispecific antibody fragments," Proceedings of the National Academy of Sciences USA, Jul. 1993, pp. 6444-6448, vol. 90.
Hudson, Peter J. and Souriau, Christelle, "Engineered antibodies," Nature Medicine, Jan. 2003, pp. 129-134, vol. 9, No. 1.
Kabat, Elvin A. et al., "Sequences of Proteins of Immunological Interest," 1991, Fifth Edition, bibliographic pages only.
Kohmoto, Shigeo et al., "Room-Temperature Discotic Nematic Liquid Crystals over a Wide Temperature Range: Alkali-Metal-Ion-Induced Phase Transition from Discotic Nematic to Columnar Phases," Journal of the American Chemical Society, 2007, pp. 13364-13365, vol. 129.
Lamansky, Sergey et al., "Synthesis and Characterization of Phosphorescent Cyclometalated Iridium Complexes," Inorganic Chemistry, 2001, pp. 1704-1711, vol. 40.
Lion, C. et al., "Synthese Dans La Serie des Phenanthridines I. Recherches des Conditions Experimentales Optimales Dans La Preparation D'Alkyl-6 Phenanthridines et de Leur Sel," Bull. Soc. Chim. Belg., 1989, pp. 557-566, vol. 98, No. 8, Abstract.
Nicolai, Eric et al., "Synthesis and Angiotensin II Receptor Antagonist Activity of C-Linked Pyrazole Derivatives," Chemical and Pharmaceutical Bulletin, 1994, pp. 1617-1630, vol. 42, No. 8.
Nonoyama, Matsuo, "Chelating C-Metallation of N-Phenylpyrazole with Rhodium(III) and Iridium(III)," Journal of Organometallic Chemistry, 1975, pp. 263-267, vol. 86.
Plueckthun, A., "Chapter 11 Antibodies from *Escherichia coli*," The Pharmacology of Monoclonal Antibodies, 1994, pp. 269-315, vol. 113, Rosenburg and Moore (Editors), Springer-Verlag, New York.
Youn, So Won and Bihn, Joon Hyung, "Trifluoroacetic acid-mediated facile construction of 6-substituted phenanthridines," Tetrahedron Letters, 2009, pp. 4598-4601, vol. 50.

\* cited by examiner

*Primary Examiner* — Joseph Kosack
(74) *Attorney, Agent, or Firm* — Roche Diagnostics Operations, Inc.

(57) ABSTRACT

Novel iridium-based Ir(III) luminescent complexes, conjugates comprising these complexes as a label and their application, for example in the electrochemiluminescence based detection of an analyte.

15 Claims, No Drawings

IRIDIUM-BASED COMPLEXES FOR ECL

CROSS-REFERENCE TO RELATED APPLICATIONS

This application is a continuation of International Application No. PCT/EP2012/051996 filed Feb. 7, 2012, which claims the benefit of European Patent Application No. 11153913.6 filed Feb. 9, 2011, the disclosures of which are hereby incorporated by reference in their entirety.

BACKGROUND OF THE DISCLOSURE

Electrogenerated chemiluminescence (also called electrochemiluminescence and abbreviated ECL) is the process whereby species generated at electrodes undergo high-energy electron-transfer reactions to form excited states that emit light. The first detailed ECL studies were described by Hercules and Bard et al. in the mid-1960s. After about 40 years of study, ECL has now become a very powerful analytical technique and is widely used in the areas of, for example, immunoassay, food and water testing, and biowarfare agent detection.

Various compounds appear to be of interest for use in organic light emitting devices (OLEDs). These compounds may be appropriate for use in solid materials, for example, or may be dissolved in organic fluids. However, no conclusion can be drawn regarding their utility in an aqueous medium as, for example, required for detection of an analyte from a biological sample.

In general ECL-based detection methods may be based on the use of water-soluble ruthenium complexes, comprising Ru(II+) as metal ion. Despite significant improvements made over the past decades, a need still exists for more sensitive electrochemiluminescence-based in vitro diagnostic assays.

SUMMARY OF THE DISCLOSURE

The present disclosure relates to novel iridium-based Ir(III) luminescent complexes, conjugates comprising these complexes as a label and their application, e.g. in the electrochemiluminescence based detection of an analyte. As described herein, it has been surprisingly found that certain iridium-based If(III+) luminescent complexes, represent very promising labels for suture high sensitive ECL-based detection methods.

According to some embodiments of the instant disclosure, an iridium-based chemiluminescent compound of Formula I is provided. Formula I:

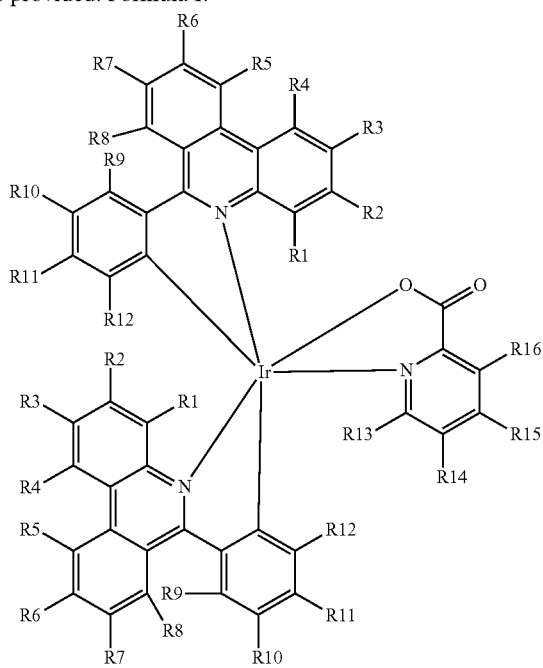

wherein R1-R16 is hydrogen, halide, cyano- or nitro-group, amino, alkylamino, substituted alkylamino, arylamino, substituted arylamino, alkylammonium, substituted alkylammonium, carboxy, carboxylic acid ester, carbamoyl, hydroxy, substituated or unsubstituated alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or R17, wherein R17 is aryl, substituted aryl, alkyl, substituted alkyl branched alkyl, substituted branched alkyl, arylalkyl, substituted arylalkyl, alkylaryl, substituted alkylaryl, alkenyl, substituted alkenyl, alkynyl, substituted alkynyl, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituated alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or, wherein within R1-R12 or/and within R13-R16, respectively, two adjacent Rs can form an aromatic ring or a substituted aromatic ring, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituted alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or, wherein within R1-R12 or/and within R13-R16, respectively, two adjacent Rs can form an aliphatic ring or a substituted aliphatic ring, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituted alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate, and wherein at least one of R13-R16 is -Q-Y, wherein Q represents a linker and Y is a functional group.

According to some embodiments, the present disclosure also discloses a conjugate comprising the above compound and covalently bound thereto an affinity binding agent.

According to some embodiments, the present disclosure further relates to the use of a compound or of a conjugate as disclosed herein for performing a luminescence measurement or an electrochemiluminescence reaction in an aqueous solution, especially, in an electro-chemiluminescent device or electrochemiluminescent detection system.

According to some further embodiments, the present disclosure provides a method for measuring an analyte by an in vitro method, the method comprising the steps of (a) providing a sample suspected or known to comprise the analyte, (b) contacting said sample with a conjugate according to the present disclosure under conditions appropriate for formation of an analyte conjugate complex, and (c) measuring the complex formed in step (b) and thereby obtaining a measure of the analyte

DETAILED DESCRIPTION OF THE EMBODIMENTS OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

The present disclosure relates to an iridium-based chemiluminescent compound of Formula I

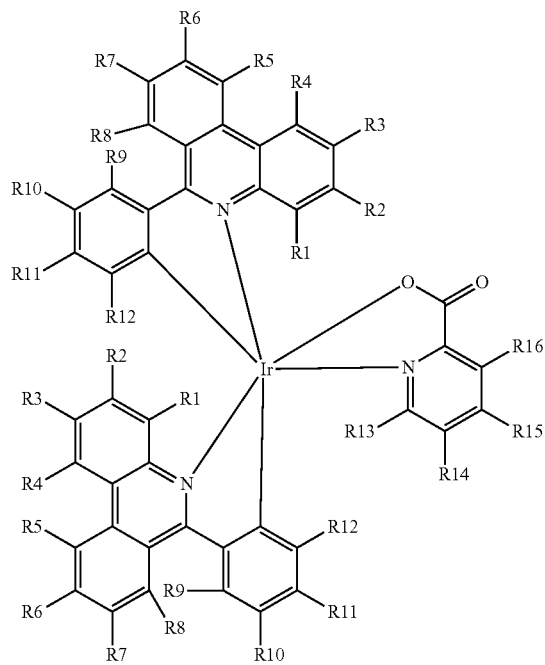

wherein R1-R16 is hydrogen, halide, cyano- or nitro-group, amino, alkylamino, substituted alkylamino, arylamino, substituted arylamino, alkylammonium, substituted alkylammonium, carboxy, carboxylic acid ester, carbamoyl, hydroxy, substituated or unsubstituated alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or R17, wherein R17 is aryl, substituted aryl, alkyl, substituted alkyl branched alkyl, substituted branched alkyl, arylalkyl, substituted arylalkyl, alkylaryl, substituted alkylaryl, alkenyl, substituted alkenyl, alkynyl, substituted alkynyl, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituated alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or, wherein within R1-R12 or/and within R13-R16, respectively, two adjacent Rs can form an aromatic ring or a substituted aromatic ring, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituted alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or, wherein within R1-R12 or/and within R13-R16, respectively, two adjacent Rs can form an aliphatic ring or a substituted aliphatic ring, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituted alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate and wherein at least one of R13-R16 is -Q-Y, wherein Q represents a linker and Y is a functional group.

In some embodiments at least one of R1 to R16 of the compound according to Formula I is substituted by at least one hydrophilic group. For example, in some embodiments, illustrative substituents for substituted alkyloxy include ethylenoxy chains comprising 1-40 ethylenoxy units, or comprising 1-20 ethylenoxy units or comprising 1-10 ethylenoxy units.

Exemplary hydrophilic groups are amino, alkylamino, with alkyl meaning a linear chain such as methyl, ethyl, propyl, butyl pentyl chain or a branched alkyl chain such as isopropyl, isobutyl, tert. butyl, for example a linear alkyl chain such as methyl or ethyl, substituted alkylamino, this contains one or two for example a branched or linear chains bound to the N-atom, which are substituted by an additional hydrophilic group such as hydroxyl or sulfo, in at least some embodiments this substituted alkylamino contains two hydroxypropyl or hydroxyethyl residues, arylamino, with aryl referring to an aromatic residue, such as phenyl, or naphthyl, substituted arylamino, with aryl as defined above and an additional residue formed by a hydrophilic group, alkylammonium, with alkyl as defined above and in some embodiments being a trimethylammonium residue or triethylammonium residue, substituted alkylammonium, carboxy, carboxylic acid ester, including an alkyl ester such as methyl or ethyl ester, carbamoyl, hydroxy, substituated or unsubstituated alkyloxy with alkyl and substituted alkyl being as defined above or aryloxy or substituted aryloxy with aryl and substituted aryl being as defined above, sulfanyl, alkylsulfonyl, arylsulfonyl, sulfo, sulfino, sulfeno, sulfonamide, sulfoxide, sulfodioxide, phosphonate, phosphinate.

According to some embodiments, such hydrophilic group is selected from amino, alkylamino, substituted alkylamino arylamino substituted arylamino, alkylammonium, substituted alkylammonium, carboxy, hydroxy, sulfo, sulfeno, sulfonamide, sulfoxide, sulfodioxide and phosphonate, where applicable, each preferably as defined in the above paragraph.

In some embodiments the hydrophilic group is selected from sulfo, sulfonamide, sulfodioxide. In an illustrative embodiment at least one of the groups R1 to R12 of Formula I is a sulfo group. In another illustrative embodiment at least one of R1 to R12 of the phenylphenantridine residues comprised in Formula I is substituted by at least one hydrophilic group. In at least some embodiments, the phenylphenantridine residues comprised in Formula I are selected from the below given substituted phenylphenantridines.

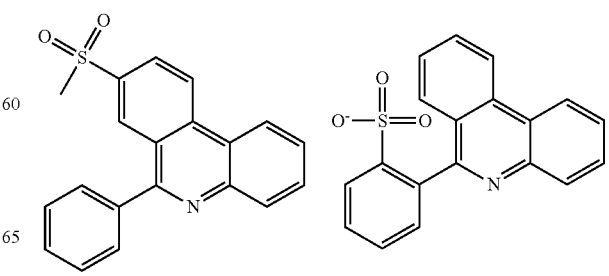

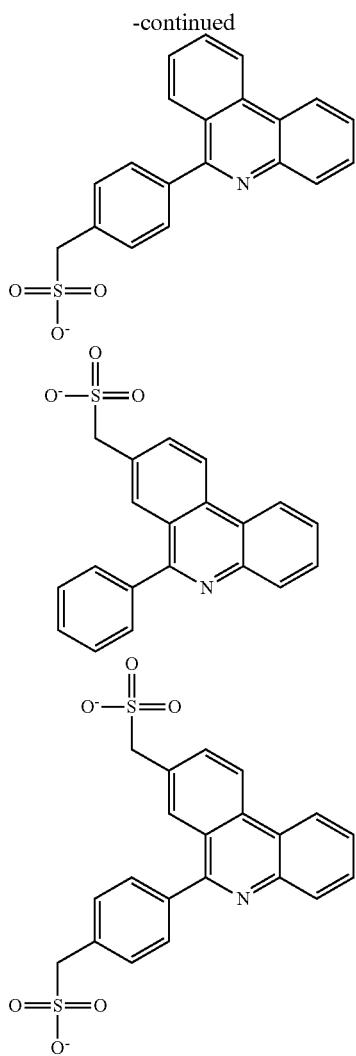

In compounds according to the present disclosure the linker Q may have a backbone length of between 1 and 20 atoms. For example, the shortest connection between the pyridyl ring of Formula I and the functional group Y may consist of 1 to 20 atoms. In an exemplary embodiment, the linker Q in the electrochemiluminescent complex of this disclosure is a straight or branched saturated, unsaturated, unsubstituted, substituted C1-C20 alkyl chain, or a C1-C20 arylalkyl chain (wherein e.g. a phenylen ring accounts for a length of four carbon atoms), or a 1 to 20 atom chain with a backbone consisting of carbon atoms and one or more heteroatoms selected from O, N and S, or a 1 to 20 atom chain with a backbone consisting of carbon atoms and one or more heteroatoms selected from O, N and S comprising at least one aryl, heteroaryl, substituted aryl or substituted heteroaryl group (wherein e.g. a phenylen ring accounts for a length of four atoms). In some embodiments the linker Q in a compound according to the present disclosure is a saturated C1-C12 alkyl chain, or a C1-C12 arylalkyl chain, or a 1 to 12 atom chain with a backbone consisting of carbon atoms and one or more heteroatoms selected from O, N and S, or a 1 to 12 atom chain with a backbone consisting of carbon atoms and one or more heteroatoms selected from O, N and S comprising at least one aryl, heteroaryl, substituted aryl or substituted heteroaryl group (wherein e.g. a phenylen ring accounts for a length of four carbon atoms).

In some embodiments the functional group Y comprised in the iridium-based complex according to the present disclosure is selected from the group consisting of carboxylic acid, N-hydroxysuccinimide ester, amino group, halogen, sulfhydryl, maleimido, alkynyl, azide, and phosphoramidite.

A conjugate comprising an iridium-based electrochemiluminescent compound of Formula I, is disclosed and defined herein, and may be covalently bound thereto a biological substance. Examples of suitable biological substances include cells, viruses, subcellular particles, proteins, lipoproteins, glycoproteins, peptides, polypeptides, nucleic acids, peptidic nucleic acids (PNA), oligosaccharides, polysaccharides, lipopoly-saccharides, cellular metabolites, haptens, hormones, pharmacological substances, alkaloids, steroids, vitamins, amino acids and sugars.

In some embodiments the biological substance of a conjugate according to the present disclosure, i.e., covalently bound to a compound according Formula I is an affinity binding agent. As the skilled artisan will appreciate in a conjugate according to the present disclosure the functional group Y of the compound according to Formula I has been used to form a covalent bond with a group on the affinity binding agent. In case an affinity binding reagent would not in itself contain an appropriate group for binding or reacting with the group Y, such group can be easily introduced into the affinity binding agent by relying on well-established procedures.

Not wishing to be limited further, but in the interest of clarity, the affinity binding agent may comprise any of the following; an antigen, a protein, an antibody, biotin or biotin analogue and avidin or streptavidin, sugar and lectin, an enzyme, a polypeptide, an amino group, a nucleic acid or nucleic acid analogue and complementary nucleic acid, a nucleotide, a polynucleotide, a peptide nucleic acid (PNA), a polysaccharide, a metal-ion sequestering agent, receptor agonist, receptor antagonist, or any combination thereof. For example, the affinity binding agent can be one partner of a specific binding pair, where the other partner of said binding pair is associated with or is the target on a cell surface or an intracellular structure.

In some illustrative embodiments, an affinity binding agent may be a partner or member of an affinity binding pair, or as it is also called by the skilled artisan, a partner or member of a specific binding pair. According to some embodiments, an affinity binding agent may hves at least an affinity of $10^7$ l/mol to its target, e.g. one member of a specific binding pair, like an antibody, to the other member of the specific binding pair, like its antigen. An affinity binding agent may also have an affinity of $10^8$ l/mol or even more such as $10^9$ l/mol for its target.

In some exemplary embodiments the present disclosure relates to a conjugate wherein the affinity binding agent is selected from the group consisting of antigen, antibody, biotin or biotin analogue, avidin or streptavidin, sugar, lectin, nucleic acid or nucleic acid analogue and complementary nucleic acid, receptor and ligand. In some further exemplary embodiments the present disclosure relates to a conjugate wherein the affinity binding agent is selected from the group consisting of antibody, biotin or biotin analogue, avidin or streptavidin, and nucleic acid. In further illustrative embodiments the conjugate according to the present disclosure comprises covalently linked a compound according to Formula I as disclosed and defined herein above and an affinity binding agent that either is an oligonucleotide or an antibody. Biotin analogues, according to the instant disclosure, include aminobiotin, iminobiotin or desthiobiotin.

The term "oligonucleotide" or "nucleic acid" as used herein, generally refers to short, generally single stranded, polynucleotides that comprise at least 8 nucleotides and at most about 1000 nucleotides. In some illustrative embodiments an oligonucleotide will have a length of at least 9, 10, 11, 12, 15, 18, 21, 24, 27 or 30 nucleotides. In some further illustrative embodiments an oligonucleotide will have a length of no more than 200, 150, 100, 90, 80, 70, 60, 50, 45, 40, 35 or 30 nucleotides. The term oligonucleotide is to be understood broadly and includes DNA and RNA as well as analogues and modification thereof.

A nucleic acid analogue may, for example, contain a substituted nucleotide carrying a substituent at the standard bases deoxyadenosine (dA), deoxyguanosine (dG), deoxycytosine (dC), deoxythymidine (dT), deoxyuracil (dU). Examples of such substituted nucleobases include: 5-substituted pyrimidines like 5 methyl dC, aminoallyl dU or dC, 5-(aminoethyl-3-acrylimido)-dU, 5-propinyl-dU or -dC, 5 halogenated-dU or -dC; N substituted pyrimidines like N4-ethyl-dC; N substituted purines like N6-ethyl-dA, N2-ethyl-dG; 8 substituted purines like 8-[6-amino)-hex-1-yl]-8-amino-dG or -dA, 8 halogenated dA or dG, 8-alkyl dG or dA; and 2 substituted dA like 2 amino dA. A nucleic acid analogue may, for example, contain a nucleotide or a nucleoside analogue (e.g., the naturally occurring nucleobases may be exchanged by using nucleobase analogs like 5-Nitroindol d riboside; 3 nitro pyrrole d riboside, deoxyinosine (dI), deoxyxanthosine (dX); 7 deaza-dG, -dA, -dI or -dX; 7-deaza-8-aza -dG, -dA, -dI or -dX; 8-aza -dA, -dG, -dI or -dX; d Formycin; pseudo dU; pseudo iso dC; 4 thio dT; 6 thio dG; 2 thio dT; iso dG; 5-methyl-iso-dC; N8-linked 8-aza-7-deaza-dA; 5,6-dihydro-5-aza-dC; and etheno-dA or pyrollo-dC). As obvious to the skilled artisan, the nucleobase in the complementary strand should be selected in such a manner that duplex formation is specific. If, for example, 5-methyl-iso-dC is used in one strand (e.g. (a)) iso dG should be in the complementary strand (e.g. (a')). Further, in a nucleic acid analogue the oligonucleotide backbone may be modified to contain substituted sugar residues, sugar analogs, modifications in the internucleoside phosphate moiety, and/or be a PNA.

According to some embodiments, an oligonucleotide may for example contain a nucleotide with a substituted deoxy ribose like 2'-methoxy, 2'-fluoro, 2'-methylseleno, 2'-allyloxy, 4'-methyl dN (wherein N is a nucleobase, e.g., A, G, C, T or U).

Sugar analogs are, for example, Xylose; 2',4' bridged Ribose like (2'-O, 4'-C methylene)- (oligomer known as LNA) or (2'-O, 4'-C ethylene)- (oligomer known as ENA); L-ribose, L- d-ribose, hexitol (oligomer known as HNA); cyclohexenyl (oligomer known as CeNA); altritol (oligomer known as ANA); a tricyclic ribose analog where C3' and C5' atoms are connected by an ethylene bridge that is fused to a cyclopropane ring (oligomer known as tricycloDNA); glycerin (oligomer known as GNA); Glucopyranose (oligomer known as Homo DNA); carbaribose (with a cyclopentan instead of a tetrahydrofuran subunit); hydroxymethyl-morpholin (oligomers known as morpholino DNA)

A number of modifications of the internucleosidic phosphate moiety are also known not to interfere with hybridization properties and such backbone modifications can also be combined with substituted nucleotides or nucleotide analogs. Examples include phosphorthioate, phosphordithioate, phosphoramidate and methylphosphonate oligonucleotides.

PNA (having a backbone without phosphate and d-ribose) can also be used as a DNA analog.

The above mentioned modified nucleotides, nucleotide analogs as well as oligonucleotide backbone modifications can be combined as desired in an oligonucleotide in the sense of the present disclosure.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light-chain and heavy-chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains generally contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains. Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The subunit structures and three-dimensional configurations of different classes of immunoglobulins are well known and described generally in, for example, Abbas et al., Cellular and Mol. Immunology, 4th ed., W.B. Saunders, Co. (2000). An antibody may be part of a larger fusion molecule, formed by covalent or non-covalent association of the antibody with one or more other proteins or peptides.

The terms "full-length antibody," "intact antibody," and "whole antibody" are used herein interchangeably to refer to an antibody in its substantially intact form, not antibody fragments as defined below. The terms particularly refer to an antibody with heavy chains that contain an Fc region.

"Antibody fragments" comprise a portion of an intact antibody, for example, such as a portion comprising the antigen-binding region thereof. Examples of antibody fragments include Fab, Fab', F(ab')2, and Fv fragments; diabodies; linear antibodies; single-chain antibody molecules; and multi-specific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields a F(ab')2 fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody-hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Single-chain Fv" or "scFv" antibody fragments comprise the VH and VL domains of an antibody, wherein these domains are present in a single polypeptide chain. Generally, the scFv polypeptide further comprises a polypeptide linker between the VH and VL domains that enables the scFv to form the desired structure for antigen binding. For a review of scFv, see, e.g., Plueckthun, In: The Pharmacology of Monoclonal Antibodies, Vol. 113, Rosenburg and Moore (eds.), Springer-Verlag, New York (1994) pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 0404 097; WO 1993/01161; Hudson, P. J. et al., Nat. Med. 9 (2003) 129-134; and Holliger, P. et al., PNAS USA 90 (1993) 6444-6448. Triabodies and tetrabodies are also described in Hudson, P. J. et al., Nat. Med. 9 (2003) 129-134.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target-binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations, which typically include different antibodies directed against different determinants (epitopes), each monoclonal antibody of a monoclonal-antibody preparation is directed against a single determinant on an antigen. In addition to their specificity, monoclonal-antibody preparations are advantageous in that they are typically uncontaminated by other immunoglobulins.

As mentioned, the compounds and conjugates as disclosed herein have quite favorable properties. For example the disclosed compounds or conjugates, respectively, show a high ECL efficiency. This high efficiency is also present if the corresponding measurements are performed in an aqueous system as compared to many, many ECL-labels that only have shown high ECL-efficiency when analyzed in an organic solvent. E.g., many OLED dyes usually are analyzed in acetonitrile and either are not soluble in an aqueous solution or, if soluble, due not show efficient electrochemiluminescence in an aqueous solution.

In some exemplary embodiments the present disclosure relates the use of a compound or of a conjugate, respectively, as disclosed in the present disclosure for performing an electrochemiluminescense reaction in an aqueous solution. According to such embodiments, an aqueous solution is any solution comprising at least 90% water (weight by weight). Obviously such aqueous solution may contain in addition ingredients like buffer compounds, detergents and for example tertiary amines like tripropylamine as electron donor in the ECL reaction.

In some embodiments, the present disclosure relates to the use of a compound or of a conjugate, respectively, as disclosed in the present disclosure in an electrochemiluminescence based detection method. In some embodiments the present disclosure relates the use of a compound or of a conjugate, respectively, as disclosed in the present disclosure in the detection of an analyte.

An analyte according to the present disclosure may be any inorganic or organic molecule, including any biological substance of interest. Examples of suitable biological substances that represent an analyte in the sense of the present disclosure are cells, viruses, subcellular particles, proteins, lipoproteins, glycoproteins, peptides, polypeptides, nucleic acids, oligosaccharides, polysaccharides, lipopoly-saccharides, cellular metabolites, haptens, hormones, pharmacological substances, alkaloids, steroids, vitamins, amino acids and sugars. According to the instant disclosure, the analyte may be selected from the group consisting of a polypeptide, a carbohydrate, and an inorganic or organic drug molecule.

A polypeptide or protein is a molecule that is essentially composed of amino acids and that has at least two amino acids linked by peptidic linkage. In case the analyte of interest to be investigated in a method disclosed here, the polypeptide may consist of at least 5, 6, 7, 8, 9, 10, 12, 15, 20, 25, and 30 to up to about 10,000 amino acids. For example, according to some embodiments the polypeptide contains from 5 to 2,000, or from 10 to 1,000 amino acids.

In case the analyte is a nucleic acid, these nucleic acids may comprise naturally occurring DNA or RNA oligonucleotides.

In some embodiments the present disclosure relates to a method for measuring an analyte by an in vitro method, the method comprising the steps of (a) providing a sample suspected or known to comprise the analyte, (b) contacting said sample with a conjugate according between an affinity binding agent and a compound according to Formula I as disclosed in the present disclosure under conditions appropriate for formation of an analyte conjugate complex, (c) measuring the complex formed in step (b) and thereby obtaining a measure of the analyte.

In some embodiments the measurement in the above method for detection of an analyte is performed by using an electrochemiluminescence based detection procedure. Also, in at least some such embodiments, the method is practiced in an aqueous solution.

The following examples, sequence listing, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure.

Illustrative Embodiments

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. An iridium-based chemiluminescent compound of Formula I

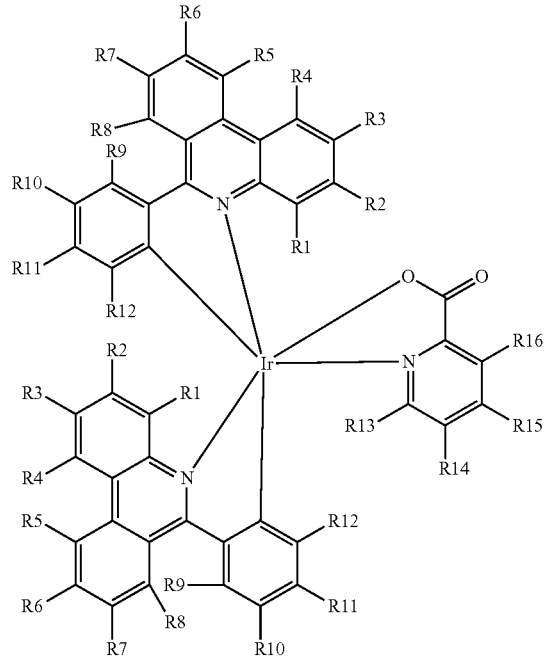

wherein R1-R16 is hydrogen, halide, cyano- or nitro-group, amino, alkylamino, substituted alkylamino, arylamino, substituted arylamino, alkylammonium, substituted alkylammonium, carboxy, carboxylic acid ester, carbamoyl, hydroxy, substituted or unsubstituated alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or R17, wherein R17 is aryl, substituted aryl, alkyl, substituted alkyl branched alkyl, substituted branched alkyl, arylalkyl, substituted arylalkyl, alkylaryl, substituted alkylaryl, alkenyl, substituted alkenyl, alkynyl, substituted alkynyl, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituated alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or, wherein within R1-R12 or/and within R13-R16, respectively, two adjacent Rs can form an aromatic ring or a substituted aromatic ring, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituted alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or, wherein within R1-R12 or/and within R13-R16, respectively, two adjacent Rs can form an aliphatic ring or a substituted aliphatic ring, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituted alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate and wherein at least one of R13-R16 is -Q-Y, wherein Q represents a linker and Y is a functional group.
2. The compound according to embodiment 1, wherein the linker Q is a straight or branched saturated, unsaturated, unsubstituted or substituted C1-C20 alkyl chain, or a 1 to 20 atom chain with a backbone consisting of carbon atoms and one or more heteroatoms selected from O, N and S.
3. The compound according to embodiment 1, wherein the linker Q is a saturated C1-C12 alkyl chain or a 1 to 12 atom chain with a backbone consisting of carbon atoms and one or more heteroatoms selected from O, N and S.
4. The compound according to embodiment 1 or 2, wherein the functional group Y is selected from the group consisting of carboxylic acid, N-hydroxysuccinimide ester, amino group, halogen, sulfhydryl, maleimido, alkynyl, azide and phosphoramidite.
5. A conjugate comprising a compound according to any of embodiments 1 to 4 and covalently bound thereto an affinity binding agent.
6. The conjugate of embodiment 5, wherein the affinity binding agent is selected from the group consisting of antigen and antibody, biotin or biotin analogue and avidin or streptavidin, sugar and lectin, nucleic acid or nucleic acid analogue and complementary nucleic acid and receptor and ligand.
7. The conjugate according to embodiment 5 or 6, wherein said affinity binding agent is a nucleic acid or an antibody.
8 Use of a compound according to any of embodiments 1 to 4 or of a conjugate according to any of embodiments 5 to 7 for performing an electrochemiluminescence reaction in an aqueous solution.
9. Use of a compound according to any of embodiments 1 to 4 or of a conjugate according to any of embodiments 5 to 7 in an electrochemiluminescence based detection method.
10. Use of a compound according to any of embodiments 1 to 4 or of a conjugate according to any of embodiments 5 to 7 in the detection of an analyte.
11. A method for measuring an analyte by an in vitro method, the method comprising the steps of
a) providing a sample suspected or known to comprise the analyte
b) contacting said sample with a conjugate according to any of embodiments 5 to 7 under conditions appropriate for formation of an analyte conjugate complex,
c) measuring the complex formed in step (b) and thereby obtaining a measure of the analyte.

EXAMPLES

Example 1

Synthesis of Substituted Phenyl-Phenanthridines

Example 1.1

General Procedure for the Synthesis of Substituted 2-Aminobiphenyls

With the Suzuki-Miyaura coupling reaction as described by Youn, S. W., in Tetrahedron Lett. 50 (2009) 4598-4601 between commercially available 2-bromoaniline derivates and the corresponding arylboronic acid the appropriate 2-aminobiphenyls can be synthesized, which are required for further reactions to phenanthridines.

Typical Procedure:

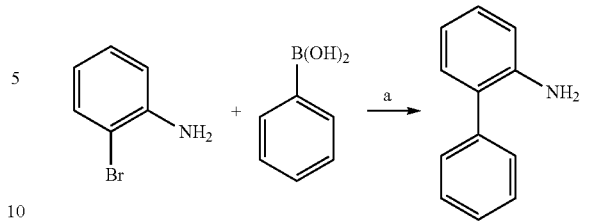

a: 10 mol % $PdCl_2(PPh_3)_2$, $K_2CO_3$, $DMF/H_2O$ (5/1), 80° C., 24 h

Other Examples

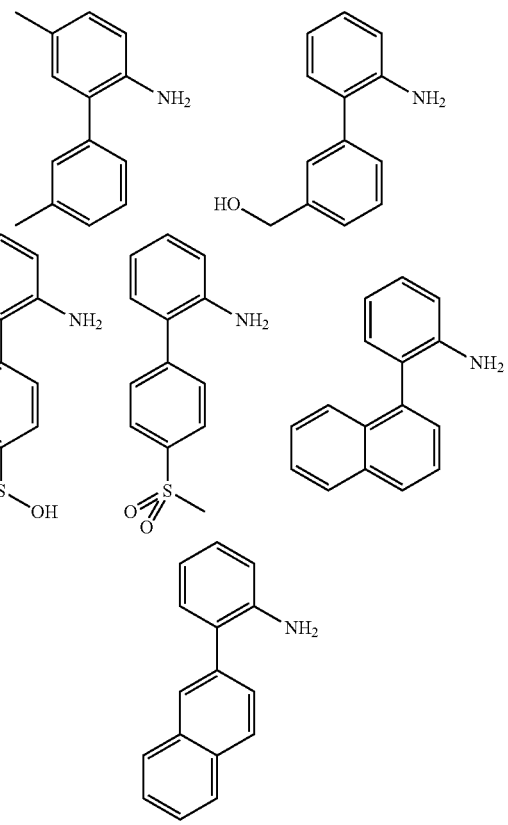

Example 1.2

General Procedure for the Synthesis of Substituted Phenanthridines

To the ice-cooled solution of 2-arylaniline 1 (0.01 mol) in chloroform (20 ml) was added aryl acid chloride 2 (0.01 mol) and stirred under inert condition for 30 min at room temperature. The resulting mixture was refluxed with stirring for the next 2 hours. The reaction mixture was treated by the dropwise addition of pyridine (0.02 mol in 10 ml chloroform) over a period of 60 minutes. The mixture was allowed to cool to room temperature and stirred overnight. The mixture was washed well with 0.5 M HCl, dried over $MgSO_4$ and concentrated in vacuum. The crude product was purified by flash chromatography on silica gel, 3:2 hexane/ethyl acetate to give pure product 3 in 66% yield.

Benzamido-2-biphenyl 3 (0.01 mol) and $POCl_3$ (5 ml) in 20 ml of toluene were refluxed and stirred under nitrogen for 18 hours, following the procedure described by Lion, C., in Bull. Soc. Chim. Belg. 98 (1989) 557-566. The cooled reaction mixture was diluted with CH$_2$Cl$_2$ (30 ml) and poured into ice, washed with 25% NH$_4$OH and distilled water. The organic layer was dried over MgSO$_4$ and concentrated in vacuo, followed by flash chromatography (silica gel, 1:1 hexane/ethyl acetate) gave the product 4,6-phenylphenanthridine.

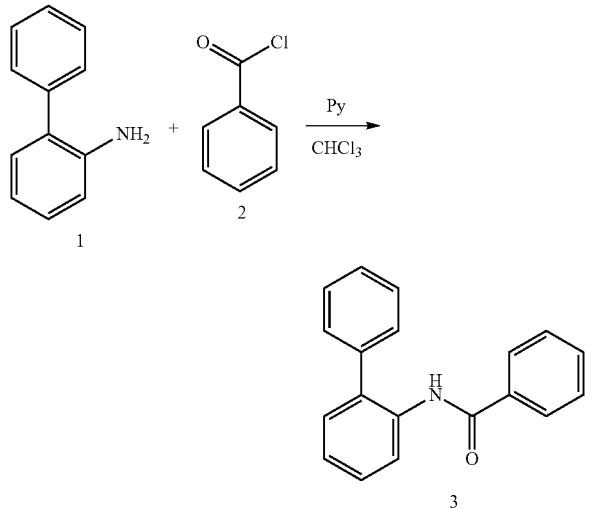

Yield: 52%. White solid. $^1$H NMR (CDCl$_3$, 400 MHz) δ 7.54-7.85 (m, 9H), 8.10 (d, J=8.0 Hz, 1H), 8.28 (d, J=7.9 Hz, 1H), 8.62 (d, J=8.4 Hz, 1H), 8.67 (d, J=8.4 Hz, 1H).

Using 2-naphthalen-2-yl-phenylamine instead of 2-arylaniline:

$^1$H-NMR (400 MHz, CDCl$_3$) δ 8.64 (d, J=9.1 Hz, 2H), 8.29 (d, J=8.1 Hz, 1H), 8.16 (d, J=8.92 Hz, 1H), 7.92 (d, J=7.48 Hz, 1H), 7.79-7.75 (m, 2H), 7.69 (t, J=14.0, 8.2 Hz, 1H), 7.63-7.61 (m, 2H), 7.53-7.46 (m, 4H), 7.19 (t, J=14.3, 7.2 Hz, 1H).

MS: [M+H]$^+$ 306.3

Using naphthalene-carbonyl chloride instead of phenyl acid chloride:

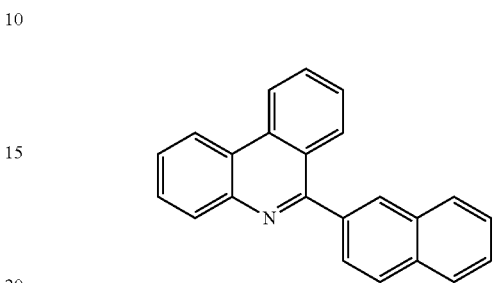

$^1$H-NMR (400 MHz, CDCl$_3$) δ 8.74 (d, J=8.3 Hz, 1H), 8.65 (d, J=8.1 Hz, 1H), 8.27 (d, J=8.1 Hz, 1H), 8.23 (s, 1H), 8.15 (d, J=8.3 Hz, 1H), 8.03 (d, J=8.4 Hz, 1H), 7.97-7.94 (m, 2H), 7.90-7.85 (m, 2H), 7.80-7.69 (m, 2H), 7.62 (t, J=14.2, 7.1 Hz, 1H), 7.59-7.55 (m, 2H)

MS: [M+H]$^+$ 306.3

Example 1.3

Procedure for the Synthesis of 6-(2-Sulfophenyl) Phenanthridine

The 6-(2-sulfophenyl)phenanthridine can be synthesized by gentle heating of arylaniline (0.01 mol) with 2-sulfobenzoic acid cyclic anhydride (0.01 mol) in CH$_3$CN for 6 hours using the procedure as described by Nicolai, E., in Chem. Pharm. Bull. 42 (1994) 1617-1630.

After purification the product can be converted to the appropriate phenanthridine based on the method described in example 1.2.

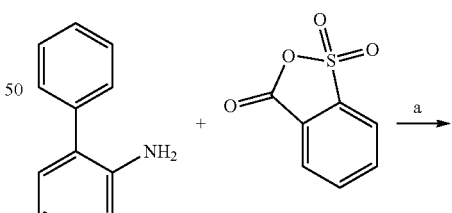

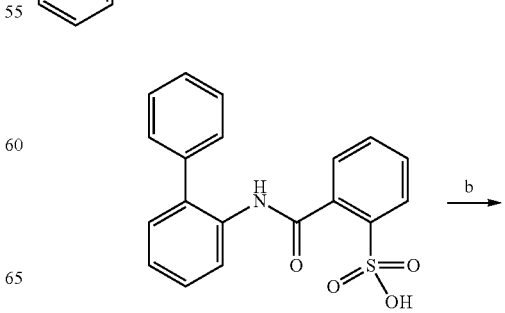

-continued

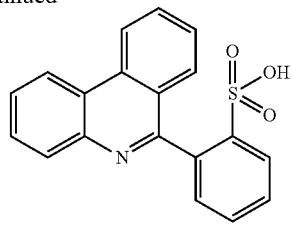

Example 1.4

Procedure for the Synthesis of 6-Phenyl-Alkylsulfonyl Phenanthridine

The 6-phenyl-alkylsulfonyl phenanthridine can be synthesized by gentle heating of alkylsulfonyl-arylaniline (0.01 mol) with benzoic acid chloride (0.01 mol) in chloroform using the procedure as described by Lion, C., in Bull. Soc. Chim. Belg. 98 (1989) 557-566, see example 1.2.

After purification the product can be converted to the appropriate phenanthridine based on the method described in example 1.2.

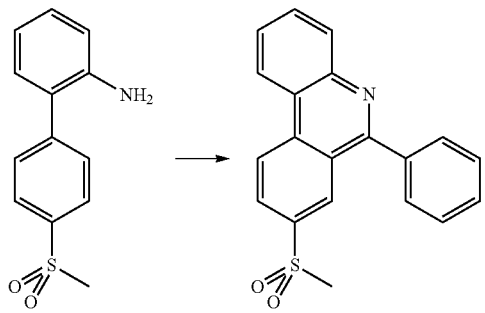 [SMILES: CS(=O)(=O)c1ccc(-c2ccccc2N)cc1 ; CS(=O)(=O)c1ccc2c(c1)c(-c1ccccc1)nc1ccccc12]

$^1$H-NMR (400 MHz, CDCl3) δ 8.92 (d, J=8.7 Hz, 1H), 8.75 (d, J=1.9 Hz, 1H), 8.68 (d, J=7.0 Hz, 1H), 8.35 (dd, J=8.7, 2.0 Hz, 1H), 8.30 (d, J=7.2 Hz, 1H), 7.89 (t, J=15.3, 7.1 Hz, 1H), 7.81-7.73 (m, 3H), 7.64-7.56 (m, 3H) 3.12 (s, 3H).
MS: [M+H]+ 334.3

The 6-(4-methylsulfophenyl)phenanthridine can be also prepared by following the procedure described by Cymerman, J., in J. Chem. Soc. (1949) 703-707.

Example 1.5

Synthesis of 6-[4-(2-{2-[2-(2-Methoxy-ethoxy)-ethoxy]-ethoxy}-ethoxy)-phenyl]-phenanthridine Synthesis of 2,5,8,11-tetraoxamidecan-13-ol tosylate Procedure: (JACS, 2007, 129, 13364) To a solution of 2,5,8,11-tetraoxamidecan-13-ol (7 g, 33.6 mmol) and triethylamine (4.9 ml, 35.3 mmol) in dry CH$_2$Cl$_2$ (100 ml), 4-toluenesulfonyl chloride (6.7 g, 35.3 mmol) and DMAP (120 mg) were added. The mixture was stirred at room temperature for 20 h. The reaction mixture was washed with 80 mL of HCl (1M) and then water. The extract was dried over anhydrous MgSO4, filtrated, and the filtrate was evaporated. The residue was used in the next step without further purification. Yield: 11.0 g (90%)

NMR: $^1$H NMR (400 MHz, CDCl$_3$) δ 7.75-7.64 (m, 2H), 7.31-7.26 (m, 2H), 4.16-4.06 (m, 2H), 3.62 (m 2H), 3.59-3.40 (m, 10H), 3.30 (s, 3H), 2.38 (s, 3H).

$^{13}$C{$^1$H} NMR (101 MHz, CDCl$_3$) δ 144.75 (s), 132.90 (s), 129.77 (s), 127.8 (s), 71.82 (s), 70.60 (s), 70.48 (s), 70.47 (s), 70.41 (s), 70.39 (s), 69.23 (s), 68.55 (s), 58.90 (s), 21.53 (s).

Synthesis of 4-PEG4-benzoic acid ethyl ester

Procedure: (JACS, 2007, 129, 13364) A mixture of compound ethyl 2,5,8,11-tetraoxatridecan-13-yl 4-methylbenzenesulfonate (8.1 g, 22.3 mmol), 4-hydroxybenzoic acid ethyl ester (3.7 g, 22.3 mmol), K2CO3 (15.4 g, 111.5 mmol) and 18-crown-6 (0.59 g, 2.2 mmol) was refluxed in acetone (120 ml) for 22 h. The reaction mixture was concentrated and extracted with ethyl acetate. The extract was washed with H2O, dried over anhydrous MgSO4, and filtrated. The filtrate was evaporated to dryness and the residue was purified by column chromatography on silica gel (dichloromethane/methanol=100:1) to obtain the compound (1.93 g, 88%). Yield: 7 g (88%)

NMR: $^1$H NMR (400 MHz, CDCl$_3$) δ 8.01-7.84 (m, 2H), 6.96-6.85 (m, 2H), 4.29 (q, J=7.1 Hz, 2H), 4.12 (dd, J=5.4, 4.3 Hz, 2H), 3.82 (dd, J=5.4, 4.2 Hz, 2H), 3.71-3.56 (m, 10H), 3.51-3.45 (m, 2H), 3.32 (s, 3H), 1.32 (t, J=7.1 Hz, 3H).

$^{13}$C{$^1$H} NMR (101 MHz, CDCl3) δ 166.29 (s), 162.47 (s), 131.45 (s), 123.01 (s), 114.11 (s), 71.90 (s), 70.84 (s), 70.60 (s), 70.59 (s), 70.58 (s), 70.48 (s), 69.51 (s), 67.54 (s), 60.57 (s), 58.98 (s), 14.35 (s).

NMS (+): [M+Na$^+$]$^+$=calc. 379.1727, found 379.1743

Synthesis of 4-PEG4-benzoic acid

Procedure: (JACS, 2007, 129, 13364) A mixture of compound ethyl 4-(2,5,8,11-tetraoxamidecan-13-yloxy)benzoate (7 g, 19.6 mmol), and KOH (2.3 g, 41.24 mmol) in 200 mL of EtOH/H2O (1:1 v/v) was reflux overnight. After cooling down, the mixture was neutralized with HCl (2N). The resulting mixture was extracted with EtOAc and evaporated to dryness. The resulting white solid was recrystallized in EtOAc/hexanes. Yield: 5.3 g (85%)

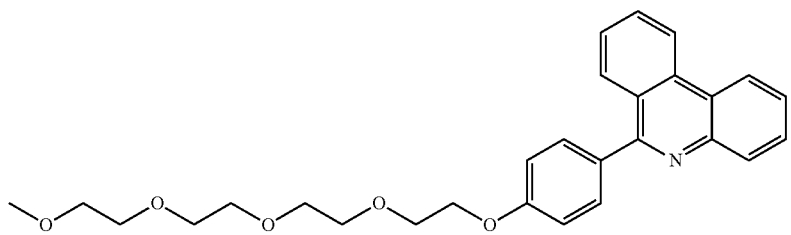 [SMILES: COCCOCCOCCOCCOc1ccc(-c2nc3ccccc3c3ccccc23)cc1]

NMR: $^1$H NMR (300 MHz, CDCl$_3$) δ 11.17 (s, 1H), 8.14-7.89 (m, 2H), 7.03-6.75 (m, 2H), 4.29-4.02 (m, 2H), 3.92-3.81 (m, 2H), 3.78-3.57 (m, 10H), 3.57-3.46 (m, 2H), 3.35 (s, 3H).

$^{13}$C{$^1$} NMR (75 MHz, CDCl3) δ 171.46 (s), 163.24 (s), 132.30 (s), 121.98 (s), 114.33 (s), 71.96 (s), 70.91 (s), 70.67 (s), 70.66 (s), 70.64 (s), 70.54 (s), 69.55 (s), 67.66 (s), 59.08 (s)

MS (−): [M−H]$^-$=calc. 327.1438, found 327.1456.

Synthesis of N-Biphenyl-2-yl-4-(2-{2-[2-(2-methoxy-ethoxy)-ethoxy]-ethoxy}-ethoxy)-benzamide Procedure: To a solution of 4-(2,5,8,11-tetraoxamidecan-13-yloxy)benzoic acid (3 g, 9.14 mmol), 0.2 mL of DMF in 30 mL dry DCM at 0° C., oxalyl chloride (1.05 mL, 12.34 mmol) was added. The reaction mixture was stirred at 0° C. for 1 h. The solution was concentrated to dryness. The oily residue was used without further purification in the next step.

A solution of 2-phenylaniline (1.6 g), pyridine (2.4 mL) in chloroform (80 mL) under inert atmosphere was cooled down to 0° C. (phenyl-4-(2,5,8,11-tetraoxamidecan-13-yloxy)benzoyl chloride (3.1 g, 9.14 mmol) in 20 mL was slowly added to the solution and the final mixture allowed to reach room temperature. The solution was reflux for 2 h and stirred overnight at room temperature. The reaction mixture was extracted with HCl (1M, 2×100 mL), NaHCO3 (100 mL) and water (50 mL). The organic phase was dried with MgSO4 and purified by chromatography in silica gel (EtOAc/hexane). Yield: 4.1 (90%)

NMR: $^1$H NMR (400 MHz, CDCl$_3$) δ 8.49 (dd, J=8.3, 0.9 Hz, 1H), 7.94 (s, 1H), 7.61-7.35 (m, 9H), 7.33-7.25 (m, 1H), 7.19 (m, 1H), 6.91-6.84 (m, 2H), 4.16-4.10 (m, 2H), 3.85 (m, 2H), 3.77-3.58 (m, 10H), 3.56-3.49 (m, 2H), 3.36 (s, 3H)

$^{13}$C{$^1$H} NMR (101 MHz, CDCl3) δ 164.56 (s), 161.65 (s), 138.18 (s), 135.12 (s), 132.32 (s), 129.97 (s), 129.39 (s), 129.22 (s), 128.66 (s), 128.57 (s), 128.16 (s), 127.13 (s), 124.18 (s), 121.23 (s), 114.57 (s), 71.95 (s), 70.89 (s), 70.64 (s), 70.63 (s), 70.54 (s), 69.54 (s), 67.63 (s), 59.04 (s), 53.51 (s).

MS (+): [M+H]$^+$=calc. 480.2386 found. 480.2383; [M+Na]$^+$=calc. 502.2200, found 502.2204

Synthesis of 6-[4-(2-{2-[2-(2-Methoxy-ethoxy)-ethoxy]-ethoxy}-ethoxy)-phenyl]-phenanthridine Procedure: N-Biphenyl-2-yl-4-(2-{2-[2-(2-methoxy-ethoxy)-ethoxy]-ethoxy}-ethoxy)-benzamide (4 g, 8.34 mmol), POCl3 (10 ml) in 10 ml toluene were refluxed for 20 h. The mixture was cooled down to room temperature, and 100 ml of dichloromethane were added. The solution was poured into ice and the mixture neutralized with NH4OH (20%). The organic phase was extracted and washed successively with destilled water and brine, and dried over MgSO4. The resulting solution was purified by flash chromatography (silica gel, in ethyl acetate/hexane 1:1, Rf=0.14). Yield: 1 g (25%)

NMR: $^1$H NMR (300 MHz, CDCl$_3$) δ 8.68 (d, J=8.3 Hz, 1H), 8.59 (dd, J=8.1, 1.4 Hz, 1H), 8.23 (dd, J=8.1, 1.1 Hz, 1H), 8.15 (dd, J=8.3, 0.7 Hz, 1H), 7.84 (ddd, J=8.3, 7.1, 1.3 Hz, 1H), 7.79-7.57 (m, 5H), 7.15-7.03 (m, 2H), 4.29-4.19 (m, 2H), 3.93-3.90 (m, 2H), 3.80-3.60 (m, 12H), 3.59-3.49 (m, 2H), 3.37 (s, 3H).

$^{13}$C{$^1$H} NMR (75 MHz, CDCl3) δ 160.92 (s), 159.45 (s), 143.84 (s), 133.59 (s), 131.26 (s), 130.61 (s), 130.26 (s), 129.05 (s), 128.90 (s), 127.19 (s), 126.85 (s), 125.39 (s), 123.70 (s), 122.29 (s), 122.01 (s), 114.68 (s), 72.02 (s), 70.97 (s), 70.74 (s), 70.72 (s), 70.69, 70.62 (s), 69.80 (s), 67.68 (s), 59.15 (s).

MS (+) JM358-F5, [M+H]$^+$ calc=462.2280, found 462.2275

Example 2

General Procedure for the Synthesis of Chloro-Cross-Linked Dimer Complex

The general procedure was published by Nonoyama, M., J. Organomet. Chem. 86 (1975) 263-267.

The iridium dimers were synthesized as follow: IrCl$_3$.3H$_2$O and 2.5 equiv of 6-phenylphenanthridine were heated at 120° C. for 18 h under nitrogen in 2-ethoxyethanol/water mixture (3:1, v/v). After being cooled to room temperature the precipitate was filtered off and successively washed with methanol and Et$_2$O, dried to afford the desired dimer.

Example 2.1

Complex with Unsubstituted Phenylphenanthridine

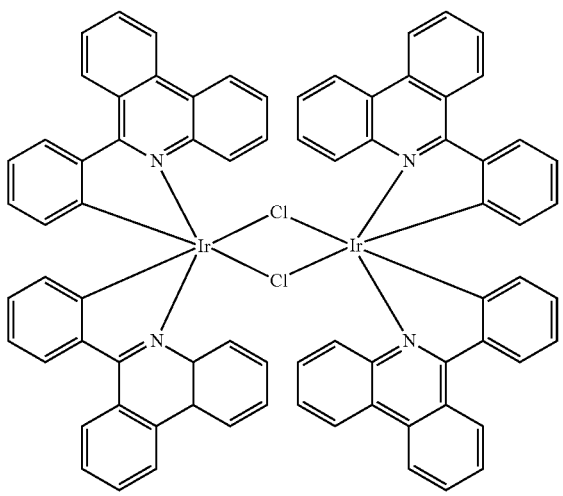

[(6-phenylphenanthridine)$_2$IrCl]2.

Yield: 71%. Brown solid. $^1$H NMR (DMSO-d$_6$, 400 MHz) δ 6.45 (d, J=6.8, 4H), 6.58 (t, J=7.1, 13.9 Hz, 4H), 6.95 (t, J=7.1, 14.2 Hz, 4H), 7.56 (t, J=7.4, 16.0 Hz, 4H), 7.68 (t, J=8.1, 16.2 Hz, 4H), 7.93 (t, J=8.0, 14.6 Hz, 4H), 8.07-8.13 (m, 8H), 8.80 (d, J=7.3 Hz, 4H), 8.93-9.01 (m, 12H).

Example 2.2

Complex with Substituted Phenylphenanthridine

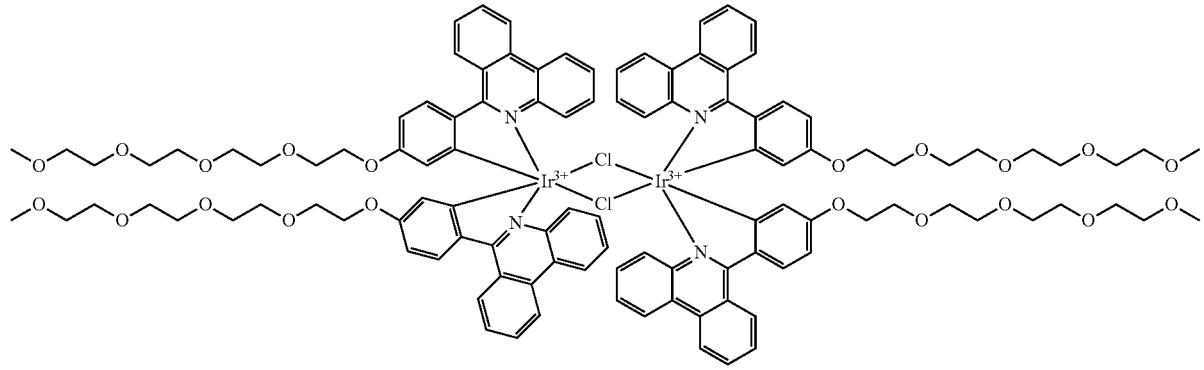

A mixture of 6-[4-(2-{2-[2-(2-Methoxy-ethoxy)-ethoxy]-ethoxy}-ethoxy)-phenyl]-phenanthridine (1 g, 2.16 mmol), $IrCl_3.3H_2O$ (346 mg, 0.98 mmol) in 16 ml of 2-EtOEtOH:$H_2O$ (12:4) was refluxed overnight under nitrogen atmosphere. The reaction mixture was cooled down to room temperature and 60 ml of water were added to obtain an oily precipitate. The supernadant was discarded and 50 ml of water were added to the residue. The mixture was stirred for 1 h to obtain a red-brownish precipitate. The solid was filtrated and washed with water (50 ml) and $Et_2O$ (30 ml). The brown solid was dissolved in the smaller amount of dichloromethane and precipitated upon addition of $Et_2O$. It was used in the next step without further purification. Yield: 550 mg (50%)

NMR: $^1$H NMR (300 MHz, CDCl3) δ 8.74 (d, J=8.1 Hz, 4H), 8.36 (dd, J=8.0, 5.2 Hz, 8H), 7.90 (dd, J=14.7, 7.7 Hz, 8H), 7.81 (d, J=9.0 Hz, 4H), 7.79-7.67 (m, 4H), 6.78-6.65 (m, 4H), 6.32 (dd, J=8.8, 2.5 Hz, 4H), 5.89-5.83 (m, 4H), 5.28 (d, J=2.5 Hz, 4H), 3.67-3.10 (m, 100H, PEG Chain, contains some impurities)

MS (ESI-MS (+)): $[M+2Na^+]^{2+}$ calc. 1171.3463, found 1171.3473; $[(CAN)_2Ir]^+$=calc. 1113.3877, found 1113.3892

Example 3

A) Synthesis of Carboxyalkylenoxy-Picolinic Acid Derivatives

A mixture of the 3-hydroxy-2-pyridinecarboxylic acid (0.01 mol), the ethyl 4-bromobutanoate or ethyl 6-bromohexanoate (0.021 mol), and a mixture of potassium carbonate (5 eq.) in DMF (20 ml) was heated at 90° C. for 20 hours under nitrogen. After cooling, the reaction mixture was poured into ice-water mixture and extracted three times with dichloromethane (30 ml), dried over anhydrous $MgSO_4$, filtered, and the solvent was evaporated to dryness. Purified by flash chromatography (silica, hexane/ethyl acetate 3:1) to afford the product (based on U.S. Pat. No. 5,219,847).

The formed ester was hydrolyzed by NaOH in MeOH (pH=10). The pH of the solution was then adjusted to 6.0 and stirred at r.t. overnight. The solvent was removed in vacuo and the residue was crystallized from hexane/acetone to give the desired product.

3-(Carboxy-pentyloxy)-pyridine-2-carboxylic acid. Yield: 51%. Gray solid. $^1$H NMR (DMSO-$d_6$, 400 MHz) δ 1.39-1.45 (m, 2H), 1.51-1.57 (m, 2H), 1.67-1.74 (m, 2H), 2.19-2.23 (m, 2H), 4.04-4.07 (m, 2H), 7.47-7.50 (m, 1H), 7.61 (d, J=8.1 Hz, 1H), 8.13 (d, J=8.1 Hz, 1H).

B) Synthesis of 5-[4-(2-Carboxy-ethyl)-phenyl]-pyridine-2-carboxylic acid

Under an argon atmosphere, to 4 ml 1,2-dimethoxyethane are added 5-bromo-pyridine-2-carboxylic acid (93 mg, 0.46 mmol), 4-(2-carboxyethyl)benzeneboronic acid (106 mg, 0.55 mmol), 0.51 ml of a 2M aqueous sodium carbonate solution and dichlorobis-(triphenylphosphin) palladium (II) (20 mg, 0.03 mmol). The mixture is stirred at 90° C. overnight, cooled and quenched with water. Ethyl acetate is added and the mixture adjusted to pH=2 with 1M hydrochloric acid. After threefold extraction with ethyl acetate, the combined organic layers are dried over magnesium sulfate, filtered, and evaporated in vacuo. The residue is purified by silica gel chromatography (eluent:dichloromethane/methanol 5:1).

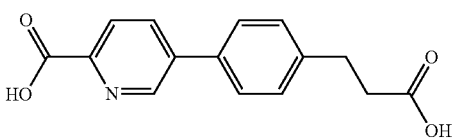 [SMILES: O=C(O)CCc1ccc(-c2ccc(C(=O)O)nc2)cc1]

$^1$H-NMR (400 MHz, DMSO-$d_6$) δ 9.00 (d, J=2 Hz, 1H), 8.25 (dd, J=8.2, 2.3 Hz, 1H), 8.11 (d, J=8.1 Hz, 1H), 7.74 (d, J=8.2 Hz, 2H), 7.41 (d, J=8.2 Hz, 2H), 2.91 (t, J=15, 7.5 Hz, 2H), 2.61 (t, J=15.1, 7.6 Hz, 2H)

MS: $[M+H]^+$ 272.3

Example 4

General Procedure for the Synthesis of Iridium Complexes

A chloro-cross-linked dimer complex 0.5 mmol, picolinate 1.25 mmol and $Na_2CO_3$ 3 mmol were mixed into 2-ethoxyethanol (12 ml) and heated at 120° C. for 15 hours. To the cooled mixture distilled water was added (25 ml), the crude product was then filtered off and washed with water, followed by portions of n-hexane and $Et_2O$. The product was purified by column chromatography (silica, n-hexane/dichloromethane) to give a red powder. (based on Lamansky, S., Inorg. Chem. 40 (2001) 1704-1711)

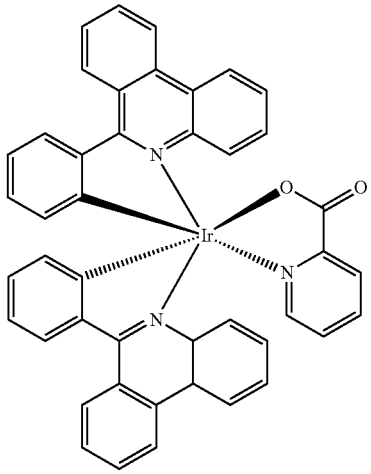

Ir(6-phenylphenanthridine)$_2$ Pyridine-2-carboxylic acid $^1$H NMR (400 MHz, CDCl$_3$) δ 9.17 (d, J=7.8 Hz, 1H), 9.09 (d, J=8.2 Hz, 1H), 8.71 (d, J=8.2 Hz, 1H), 8.62 (t, J=14.8, 7.8 Hz, 2H), 8.43-8.33 (m, 4H), 8.23 (d, J=8.1 Hz, 1H), 7.92-7.77 (m, 4H), 7.65 (t, J=15, 7.9 Hz, 2H), 7.57-7.46 (m, 3H), 7.36 (t, J=14.8, 7.8 Hz, 1H), 7.19-7.16 (m, 2H), 7.10 (d, J=7.8 Hz, 1H), 7.04 (t, J=14.2, 6.8 Hz, 1H), 6.92 (t, J=14.1, 6.7 Hz, 1H), 6.80 (t, J=13.7, 6.8 Hz, 1H), 6.67 (t, J=13.7, 6.6 Hz, 1H), 6.51 (d, J=6.8 Hz, 1H).
MS: [M+H]$^+$ 826.4

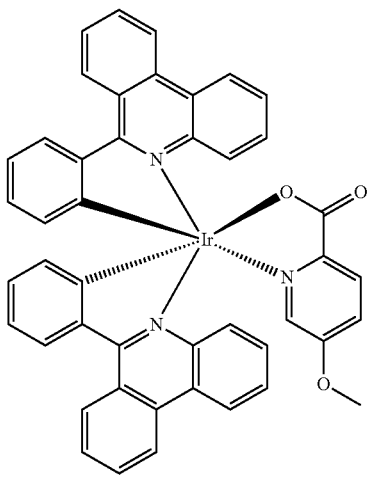

Ir(6-phenylphenanthridine)$_2$ 5-(Methoxy)pyridine-2-carboxylic acid $^1$H-NMR (400 MHz, CDCl3) δ 9.15 (d, J=8.2 Hz, 1H), 9.09 (d, J=8.2 Hz, 1H), 8.70 (d, J=7.8 Hz, 1H), 8.61 (d, J=8.2 Hz, 2H), 8.44-8.35 (m, 3H), 8.21 (d, J=8.0 Hz, 1H), 7.97 (d, J=2.7, 1H), 7.91-7.86 (m, 2H), 7.82-7.80 (m, 2H), 7.68 (d, J=8.6 Hz, 1H), 7.57-7.53 (m, 3H), 7.36 (t, J=15.2, 7.2 Hz, 1H), 7.14 (t, J=15.1, 7.6 Hz, 1H), 7.08-6.93 (m, 4H), 6.78 (t, J=14.9, 7.6 Hz, 1H), 6.65 (t, J=14.8, 7.6 Hz, 1H), 6.49 (d, J=7.6 Hz, 1H), 3.63 (s, 3H)
MS: [M+H]$^+$ 854.2

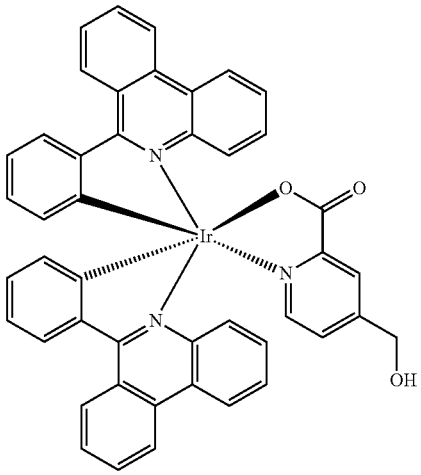

Ir(6-phenylphenanthridine)$_2$ 4-(Hydroxymethyl)pyridine-2-carboxylic acid $^1$H-NMR (400 MHz, DMSO-d$_6$) δ 9.14 (d, J=8.1 Hz, 2H), 8.96 (d, J=8.0 Hz, 1H), 8.87 (d, J=7.7 Hz, 1H), 8.73 (d, J=7.7 Hz, 1H), 8.68 (d, J=7.8 Hz, 1H), 8.51 (d, J=8.6 Hz, 1H), 8.37 (d, J=8.2 Hz, 1H), 8.26-8.24 (m, 2H), 8.10 (t, J=14.7, 7.3 Hz, 1H), 8.02-7.96 (m, 3H), 7.68 (d, J=8.4 Hz, 1H), 7.62 (t, J=15.2, 7.1 Hz, 1H), 7.53-7.48 (m, 2H), 7.39-7.37 (m, 2H), 7.16 (t, J=15.3, 7.2 Hz, 1H), 7.10-7.04 (m, 2H), 6.86 (d, J=6.8 Hz, 1H), 6.78 (t, J=14.2, 7.1 Hz, 1H), 6.67 (t, J=14.9, 7.3 Hz, 1H), 6.35 (d, J=6.8 Hz, 1H), 5.32 (s, 1H), 4.33 (s, 2H).
MS: [M+H]$^+$ 854.2

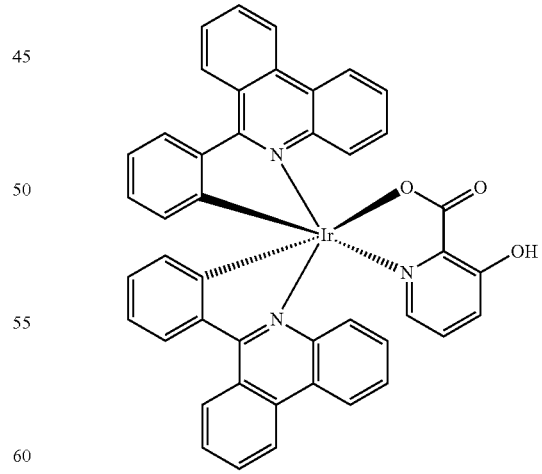

Ir(6-phenylphenanthridine)$_2$ 3-Hydroxypyridine-2-carboxylic acid $^1$H-NMR (400 MHz, CDCl$_3$) δ 9.15 (d, J=8.3 Hz, 1H), 9.06 (d, J=8.2 Hz, 1H), 8.65-8.57 (m, 3H), 8.46-8.41 (m, 2H), 8.34

(d, J=8.0 Hz, 1H), 8.21 (d, J=8.0 Hz, 1H), 7.94-7.78 (m, 5H), 7.72 (d, J=7.8 Hz, 1H), 7.58-7.55 (m, 2H), 7.40 (t, J=14.0, 7.0 Hz, 1H), 7.15 (t, J=15.2, 7.0 Hz, 1H), 7.05-6.95 (m, 5H), 6.77 (t, J=13.7, 7.0 Hz, 1H), 6.66 (t, J=13.6, 6.4 Hz, 1H), 6.50 (d, J=6.6 Hz, 1H).

MS: [M+H]⁺ 839.2

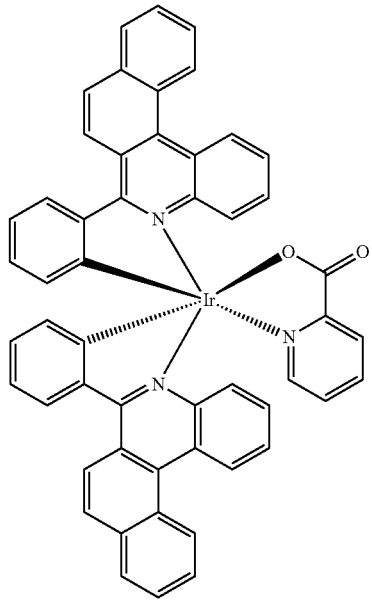

Ir(6-phenyl-benzophenanthridine)₂
Pyridine-2-carboxylic acid

¹H NMR (400 MHz, CDCl₃) δ 9.04 (m, 4H), 8.82 (m, 2H), 8.77-8.70 (m, 1H), 8.41 (d, J=8.0 Hz, 1H), 8.29-8.27 (m, 2H), 8.15-8.09 (m, 4H), 7.85 (d, J=8.3 Hz, 1H), 7.78-7.71 (m, 4H), 7.65 (d, J=7.7 Hz, 1H), 7.62-7.553 (m, 2H), 7.45-7.40 (m, 2H), 7.23-7.17 (m, 1H), 7.13-7.05 (m, 3H), 7.05-7.00 (m, 1H), 6.83 (dd, J=10.8, 4.0 Hz, 1H), 6.68 (dd, J=10.9, 3.8 Hz, 1H), 6.51 (dd, J=7.6, 0.9 Hz, 1H).

MS: [M+H]⁺ 924.2

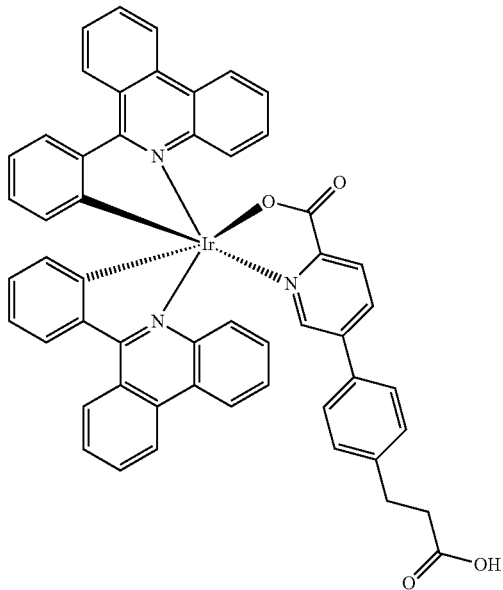

Ir(6-phenylphenanthridine)₂ 2-(Carboxyethyl-phenyl)pyridine-2-carboxylic acid

¹H-NMR (400 MHz, DMSO-d₆) δ 9.24 (m, 1H), 9.15 (d, J=8.0 Hz, 1H), 8.97 (d, J=8.4 Hz, 1H), 8.88 (d, J=8.1 Hz, 1H), 8.73 (d, J=7.6 Hz, 1H), 8.68 (d, J=7.4 Hz, 1H), 8.50 (d, J=7.8 Hz, 1H), 8.45 (d, J=7.9 Hz, 1H), 8.34 (d, J=2.0 Hz, 1H), 8.28 (d, J=7.9 Hz, 1H), 8.13-8.00 (m, 4H), 7.92 (dd, J=8.1, 2.1 Hz, 1H), 7.63 (t, J=15.2, 7.0 Hz, 2H), 7.54-7.42 (m, 3H), 7.35 (d, J=8.2 Hz, 2H), 7.17 (t, J=15.2, 7.0 Hz, 1H), 7.10-7.06 (m, 3H), 7.02 (t, J=15.7, 7.3 Hz, 1H), 6.89 (d, J=6.7 Hz, 1H), 6.77 (t, J=14.0, 7.1 Hz, 1H), 6.71 (t, J=14.8, 7.0 Hz, 1H), 6.45 (d, J=6.7 Hz, 1H), 2.86 (t, J=15.2, 7.5 Hz, 2H), 2.55 (t, J=15.4, 7.7 Hz, 2H).

MS: [M+H]⁺ 972.3

Synthesis of JM 360

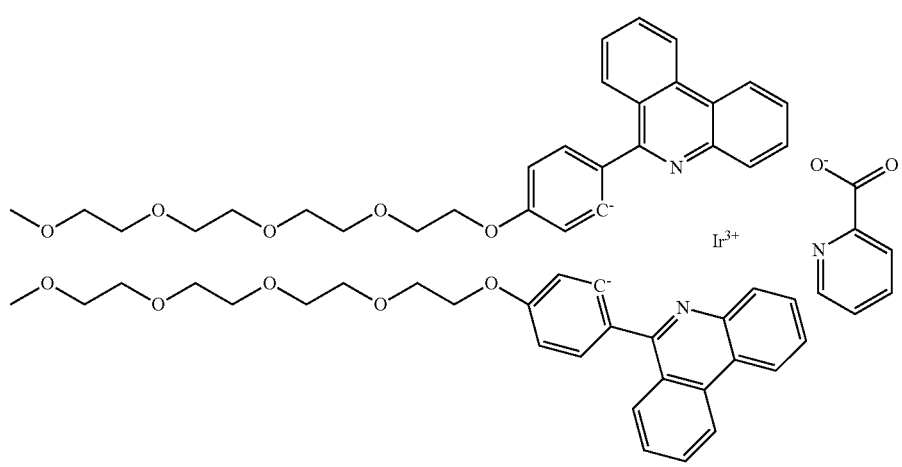

JM 360

A suspension of Ir-dimer (150 mg, 0,065 mmol), picolinic acid (17 mg, 0.137 mmol) and Na$_2$CO$_3$ (70 mg, 0.65 mmol) in 20 mL dichloromethane/ethanol (4:1) was refluxed overnight. After cooling down, the mixture was concentrated to dryness. The residue was purified by flash cromatography in dichloromethane/MeOH (gradient from 100:0 to 10:1). The compound was recrystallized in dichloromethane/Et$_2$O. Yield: 30%.

NMR: $^1$H NMR (300 MHz, CDCl$_3$) δ 9.06 (d, J=8.2 Hz, 1H), 8.98 (d, J=8.1 Hz, 1H), 8.61 (m, 3H), 8.46-8.21 (m, 4H), 8.13 (d, J=8.9 Hz, 1H), 7.83 (m, 4H), 7.61 (m, 2H), 7.57-7.41 (m, 3H), 7.30 (d, J=7.2 Hz, 1H), 7.24-7.12 (m, 1H), 6.89 (t, J=7.2 Hz, 1H), 6.76 (dd, J=8.9, 2.5 Hz, 1H), 6.61 (dd, J=8.8, 2.6 Hz, 1H), 6.54 (d, J=2.5 Hz, 1H), 5.99 (d, J=2.6 Hz, 1H), 3.85-3.41 (m, 32H), 3.34 (s, 3H), 3.33 (s, 3H).

MS: [2M+2Na]$^{2+}$ calc. 1258.4012, found 1258.4030. [M+H]$^+$ calc. 1236.4197, found 1236.4227

Example 5

ECL with a Novel Iridium Complex

The electrochemiluminescence signal of several metal complexes was assessed in an ELECSYS® analyzer (Roche Diagnostics GmbH). Measurements were carried out homogeneously in the absence of streptavidin-coated paramagnetic microparticles. Stock solutions of each metal complex at 0.1 mg/ml DMSO were diluted with PBS buffer resulting in 10 nM solutions. The 10 nM solutions were handled as samples on the ELECSYS® analyzer. 20 µl sample was incubated together with 90 µl Reagent 1 (ProCell) and 90 µl Reagent 2 (ProCell) for 9 min at 37° C. and subsequently the electrochemiluminescence signal was quantified.

ECL Results:
Reference Ru(bpy)3=10000 counts in 10 nmolar concentration
JM 360=31258 counts 10 nmolar concentration
RC 72=45512 count in 10 nmolar concentration

RC 72

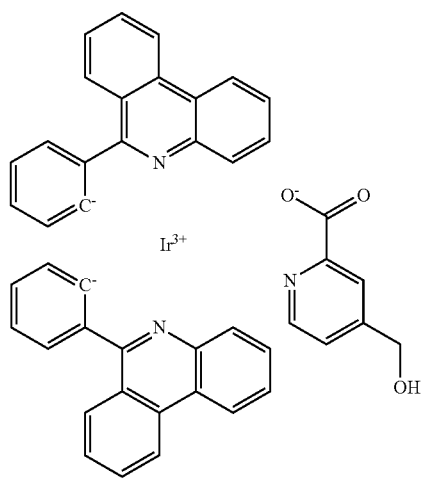

Example 6

Synthesis of an Iridium Complex with Reactive Group for Bioconjugation

Ir(6-phenylphenanthridine)$_2$ 2-(Carboxyethyl-phenyl)pyridine-2-carboxylic acid (15 mg) was dissolved in a mixture of dry acetonitrile 5 mL and dry pyridine 0.01 mL. Disuccinimidyl carbonate (DSC) (1.5 eq) was added and the mixture was stirred under nitrogen at room temperature overnight. The solution was added to chloroform (10 mL), washed with 0.5 M HCl (1×2 mL), saturated aqueous NaHCO$_3$ (1×2 mL) and water (2×5 mL) dried over MgSO$_4$, and concentrated in vacuo to yield a red powder.

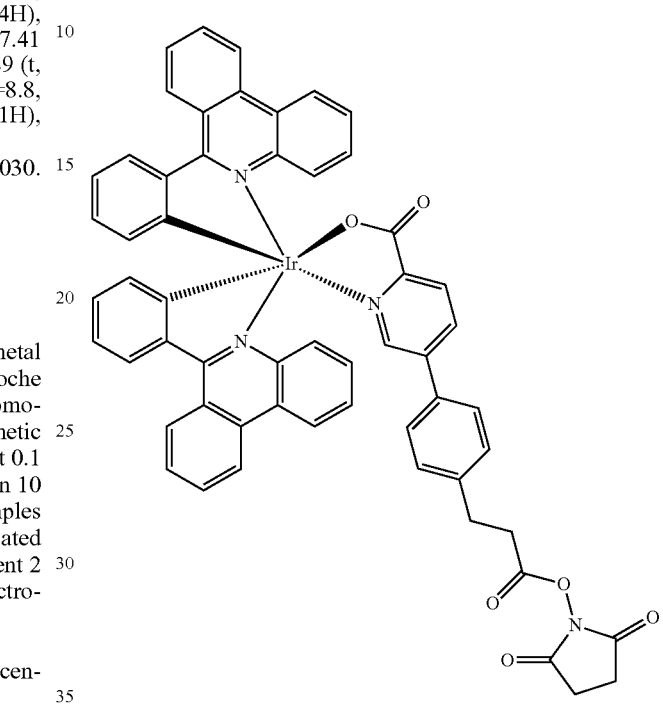

Ir(6-phenylphenanthridine)$_2$ 2-(Carboxyethyl-phenyl)pyridine-2-carboxylic acid N-succinimidyl ester $^1$H-NMR (400 MHz, CD$_3$CN) δ 9.25 (m, 1H), 9.17 (d, J=8.0 Hz, 1H), 8.83 (d, J=8.4 Hz, 1H), 8.75-8.68 (m, 1H), 8.60-8.54 (m, 3H), 8.47 (d, J=8.1 Hz, 1H), 8.43 (d, J=2.1 Hz, 1H), 8.30 (d, J=8.1 Hz, 1H), 8.06 (t, J=15.4, 7.2 Hz, 1H), 7.97-7.95 (m, 3H), 7.77-7.70 (m, 2H), 7.61 (t, J=15.2, 7.0 Hz, 1H), 7.52-7.44 (m, 3H), 7.36 (d, J=8.3 Hz, 2H), 7.18 (t, J=15.2, 7.0 Hz, 1H), 7.12-7.09 (m, 3H), 7.04-6.98 (m, 2H), 6.78 (t, J=14.9, 7.2 Hz, 1H), 6.71 (t, J=14.8, 7.5 Hz, 1H), 6.57 (d, J=7.6 Hz, 1H), 3.07-3.01 (m, 4H), 2.80 (s, 4H).

MS: [M+H]$^+$ 1069.3

Example 7

Synthesis of an Iridium-Complex Conjugate with Biotin

Ir(6-phenylphenanthridine)$_2$ 2-(Carboxyethyl-phenyl)pyridine-2-carboxylic acid NHS ester (12 mg) and 4 mg of N-Biotinyl-3,6-dioxaoctane-1,8-diamine trifluoroacetate was dissolved in a dry DMF 5 mL. Pyridine (0.016 mL in 2 mL DMF) was added and the mixture was stirred under nitrogen at room temperature overnight. The solution was added to chloroform (10 mL), washed with 0.5 M HCl (1×2 mL), saturated aqueous NaHCO$_3$ (1×2 mL) and water (2×5 mL) dried over MgSO$_4$, and concentrated in vacuo to yield a red powder. The product was purified by column chromatography (silica, n-hexane/ethyl acetate) to give red powder.

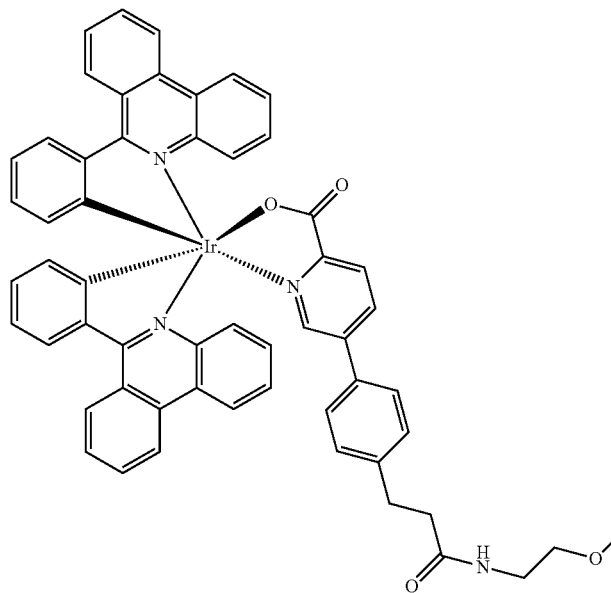

MS: [M+H]$^+$ 1328.6

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. An iridium-based chemiluminescent compound of Formula I

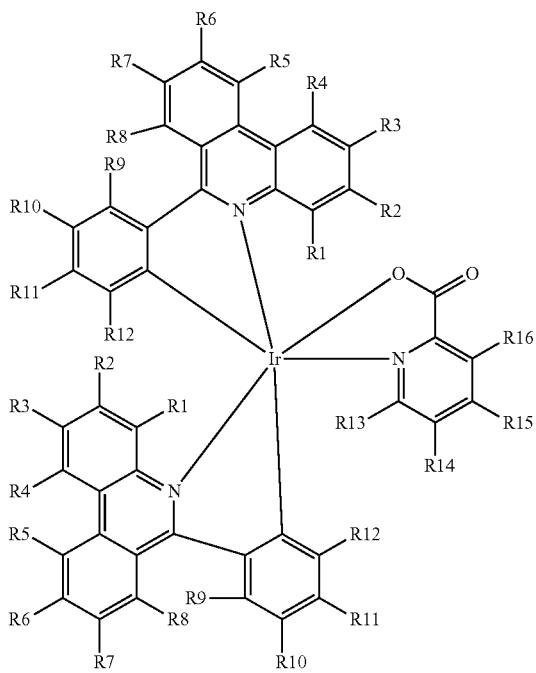

wherein R1-R16 is hydrogen, halide, cyano- or nitro-group, amino, alkylamino, substituted alkylamino, arylamino, substituted arylamino, alkylammonium, substituted alkylammonium, carboxy, carboxylic acid ester, carbamoyl, hydroxy, substituated or unsubstituated alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or R17, wherein R17 is aryl, substituted aryl, alkyl, substituted alkyl branched alkyl, substituted branched alkyl, arylalkyl, substituted arylalkyl, alkylaryl, substituted alkylaryl, alkenyl, substituted alkenyl, alkynyl, substituted alkynyl, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituated alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or, wherein within R1-R12 and/or within R13-R16, respectively, two adjacent Rs can form an aromatic ring or a substituted aromatic ring, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituted alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or, wherein within R1-R12 or/and within R13-R16, respectively, two adjacent Rs can form an aliphatic ring or a substituted aliphatic ring, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituted alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate, wherein at least one of R13-R16 is -Q-Y,
wherein Q represents a linker, wherein the linker Q is a straight or branched saturated, unsaturated, unsubstituted or substituted C1-C20 alkyl chain, or a 1 to 20 atom chain with a backbone consisting of carbon atoms and one or more heteroatoms selected from O, N and S, and Y is a functional group.

2. The compound according to claim 1, wherein the linker Q is a saturated C1-C12 alkyl chain or a 1 to 12 atom chain with a backbone consisting of carbon atoms and one or more heteroatoms selected from O, N and S.

3. A conjugate comprising a compound according to claim 1 and covalently bound thereto an affinity binding agent.

4. The conjugate of claim 3, wherein the affinity binding agent is selected from the group consisting of antigen and antibody, biotin or biotin analogue and avidin or streptavidin, sugar and lectin, nucleic acid or nucleic acid analogue and complementary nucleic acid and receptor and ligand.

5. The conjugate according to claim 3, wherein said affinity binding agent is a nucleic acid or an antibody.

6. A method for measuring an analyte by an in vitro method, the method comprising the steps of
   a) providing a sample suspected or known to comprise the analyte;
   b) contacting said sample with a conjugate of claim 3 under conditions appropriate for formation of an analyte conjugate complex; and
   c) measuring the complex formed in step (b) and thereby obtaining a measure of the analyte.

7. The methof of claim 6, wherein said step of contacting is performed in an aqueous solution.

8. The method of claim 6, wherein the affinity binding agent is selected from the group consisting of antigen and antibody, biotin or biotin analogue and avidin or streptavidin, sugar and lectin, nucleic acid or nucleic acid analogue and complementary nucleic acid and receptor and ligand.

9. The method of claim 6, wherein the affinity binding agent of the conjugate is a nucleic acid or an antibody.

10. An iridium-based chemiluminescent compound of Formula I

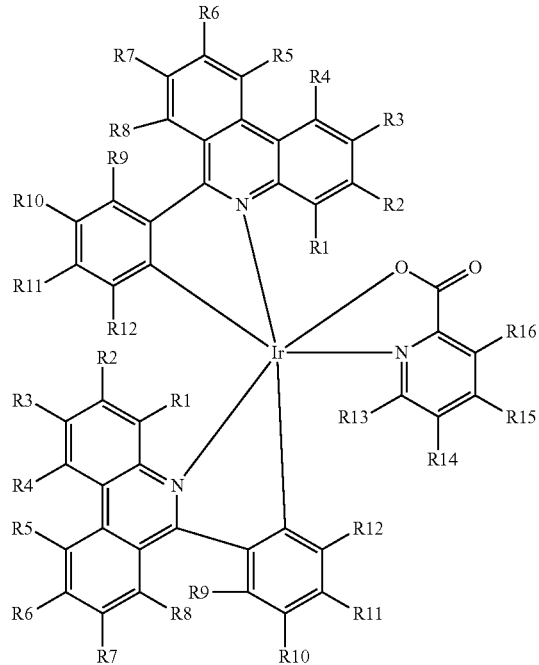

wherein R1-R16 is hydrogen, halide, cyano- or nitro-group, amino, alkylamino, substituted alkylamino, arylamino, substituted arylamino, alkylammonium, substituted alkylammonium, carboxy, carboxylic acid ester, carbamoyl, hydroxy, substituated or unsubstituated alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or R17, wherein R17 is aryl, substituted aryl, alkyl, substituted alkyl branched alkyl, substituted branched alkyl, arylalkyl, substituted arylalkyl, alkylaryl, substituted alkylaryl, alkenyl, substituted alkenyl, alkynyl, substituted alkynyl, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituated alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or, wherein within R1-R12 and/or within R13-R16, respectively, two adjacent Rs can form an aromatic ring or a substituted aromatic ring, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituted alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate or, wherein within R1-R12 or/and within R13-R16, respectively, two adjacent Rs can form an aliphatic ring or a substituted aliphatic ring, wherein the substituent is selected from hydrogen, halide, cyano- or nitro-group, a hydrophilic group, like amino, alkylamino, substituted alkylamino, alkylammonium, substituted alkylammonium, carboxy, carboxylic acid ester, carbamoyl, hydroxy, substituted or unsubstituted alkyloxy, substituted or unsubstituted aryloxy, sulfanyl, alkylsulfonyl, arylsulfonyl, sulfo, sulfino, sulfeno, sulfonamide, sulfoxide, sulfodioxide, phosphonate, phosphinate, wherein at least one of R13-R16 is -Q-Y,
wherein Q represents a linker, and
Y is a functional group selected from the group consisting of carboxylic acid, N-hydroxysuccinimide ester, amino group, halogen, sulfhydryl, maleimido, alkynyl, azide and phosphoramidite.

11. The compound according to claim 10, wherein the linker Q is a straight or branched saturated, unsaturated, unsubstituted or substituted C1-C20 alkyl chain, or a 1 to 20 atom chain with a backbone consisting of carbon atoms and one or more heteroatoms selected from O, N and S.

12. The compound according to claim 10, wherein the linker Q is a saturated C1-C12 alkyl chain or a 1 to 12 atom chain with a backbone consisting of carbon atoms and one or more heteroatoms selected from O, N and S.

13. A conjugate comprising a compound according to claim 10 and covalently bound thereto an affinity binding agent.

14. The conjugate of claim 13, wherein the affinity binding agent is selected from the group consisting of antigen and antibody, biotin or biotin analogue and avidin or streptavidin, sugar and lectin, nucleic acid or nucleic acid analogue and complementary nucleic acid and receptor and ligand.

15. The conjugate according to claim 13, wherein said affinity binding agent is a nucleic acid or an antibody.

* * * * *